(12) United States Patent
Naito et al.

(10) Patent No.: US 10,610,201 B2
(45) Date of Patent: Apr. 7, 2020

(54) ULTRASONIC PROBE AND ULTRASONIC DIAGNOSTIC APPARATUS

(71) Applicant: Konica Minolta, Inc., Tokyo (JP)

(72) Inventors: Tatsuya Naito, Tokyo (JP); Koetsu Saito, Osaka (JP); Hisashi Minemoto, Hirakata (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/414,349

(22) Filed: May 16, 2019

(65) Prior Publication Data

US 2019/0388058 A1   Dec. 26, 2019

(30) Foreign Application Priority Data

Jun. 21, 2018   (JP) .................................. 2018-117858

(51) Int. Cl.
*A61B 8/04*   (2006.01)
*A61B 8/00*   (2006.01)

(52) U.S. Cl.
CPC .......... *A61B 8/4444* (2013.01); *A61B 8/4272* (2013.01); *A61B 8/56* (2013.01); *A61B 8/4483* (2013.01)

(58) Field of Classification Search
None
See application file for complete search history.

(56) References Cited

U.S. PATENT DOCUMENTS

| | | | | |
|---|---|---|---|---|
| 8,319,399 | B2* | 11/2012 | Saito | A61B 8/4281 310/334 |
| 2009/0069691 | A1* | 3/2009 | Saito | B06B 1/0622 600/459 |
| 2015/0372219 | A1* | 12/2015 | Yamashita | H01L 41/41 310/334 |
| 2017/0196538 | A1* | 7/2017 | Sato | A61B 8/12 |

FOREIGN PATENT DOCUMENTS

JP   2001-285995 A   10/2001

* cited by examiner

*Primary Examiner* — J. San Martin
(74) *Attorney, Agent, or Firm* — Lucas & Mercanti, LLP (57) ABSTRACT

An ultrasonic probe includes: a piezoelectric element that transmits and receives an ultrasonic wave; one or a plurality of acoustic matching layers disposed on a subject side of the piezoelectric element; and a conductor layer that applies a voltage to the piezoelectric element, wherein the conductor layer is disposed between the piezoelectric element and the acoustic matching layer, or between the plurality of acoustic matching layers, a magnitude of an acoustic impedance of the conductor layer is between a magnitude of an acoustic impedance of a layer disposed on one surface side of the conductor layer and a magnitude of an acoustic impedance of a layer disposed on the other surface side of the conductor layer, and the conductor layer has a Vickers hardness (Hv) of 50 or more and 600 or less.

10 Claims, 4 Drawing Sheets

ULTRASONIC PROBE AND ULTRASONIC DIAGNOSTIC APPARATUS

The entire disclosure of Japanese patent Application No. 2018-117858, filed on Jun. 21, 2018, is incorporated herein by reference in its entirety.

BACKGROUND

Technological Field

The present invention relates to an ultrasonic probe and an ultrasonic diagnostic apparatus including the ultrasonic probe.

Description of the Related Art

By applying an ultrasonic probe connected to an ultrasonic diagnostic apparatus or communicable with the ultrasonic diagnostic apparatus to a body surface of a subject including human being and other animals or inserting the ultrasonic probe into the body, the ultrasonic diagnostic apparatus can obtain the shape, movement, or the like of a tissue as an ultrasonic diagnostic image. The ultrasonic diagnostic apparatus can repeatedly perform an examination advantageously because of high safety.

The ultrasonic probe incorporates, for example, a piezoelectric element that transmits and receives an ultrasonic wave. The piezoelectric element receives an electric signal (transmission signal) from the ultrasonic diagnostic apparatus, converts the received transmission signal into an ultrasonic signal to transmit the ultrasonic signal, receives an ultrasonic wave reflected in a living body to convert the ultrasonic wave into an electric signal (reception signal), and transmits the reception signal converted into the electric signal to the ultrasonic diagnostic apparatus.

The ultrasonic probe usually has an acoustic matching layer having an acoustic impedance with a magnitude between an acoustic impedance of the piezoelectric element and an acoustic impedance of a living body on a living body side of the piezoelectric element. The acoustic matching layer matches an acoustic impedance between the piezoelectric element and a subject (living body), and can make resolution of an ultrasonic diagnostic image to be obtained higher.

JP 2001-285995 A describes an ultrasonic probe having a conductor layer for applying a voltage to a piezoelectric element disposed between the piezoelectric element and an acoustic matching layer. According to JP 2001-285995 A, by disposing the conductor layer between the piezoelectric element and the acoustic matching layer, a range of selection of a material that can be used as the acoustic matching layer is broadened, and it is possible to manufacture the acoustic matching layer having an acoustic impedance capable of obtaining an ultrasonic diagnostic image with higher resolution. In addition, JP 2001-285995 A describes that the conductor layer may be formed of any material such as copper, nickel, aluminum, gold, or silver as long as having a small electric resistance.

As described in JP 2001-285995 A, if a conductor layer is disposed between a piezoelectric element and an acoustic matching layer and a material of the acoustic matching layer is appropriately selected, it is expected that an ultrasonic diagnostic image with higher resolution will be obtained. However, there is still a demand for further enhancing resolution of an ultrasonic diagnostic image. Therefore, development of an ultrasonic probe that can obtain an ultrasonic diagnostic image with higher image quality has been demanded.

SUMMARY

An object of the present invention is to provide an ultrasonic probe capable of enhancing the image quality of a diagnostic image and an ultrasonic diagnostic apparatus including the ultrasonic probe.

To achieve the abovementioned object, according to an aspect of the present invention, an ultrasonic probe reflecting one aspect of the present invention comprises: a piezoelectric element that transmits and receives an ultrasonic wave; one or a plurality of acoustic matching layers disposed on a subject side of the piezoelectric element; and a conductor layer that applies a voltage to the piezoelectric element, wherein the conductor layer is disposed between the piezoelectric element and the acoustic matching layer, or between the plurality of acoustic matching layers, a magnitude of an acoustic impedance of the conductor layer is between a magnitude of an acoustic impedance of a layer disposed on one surface side of the conductor layer and a magnitude of an acoustic impedance of a layer disposed on the other surface side of the conductor layer, and the conductor layer has a Vickers hardness (Hv) of 50 or more and 600 or less.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

[First Embodiment]

(Configuration of Ultrasonic Probe)

Figure 1:
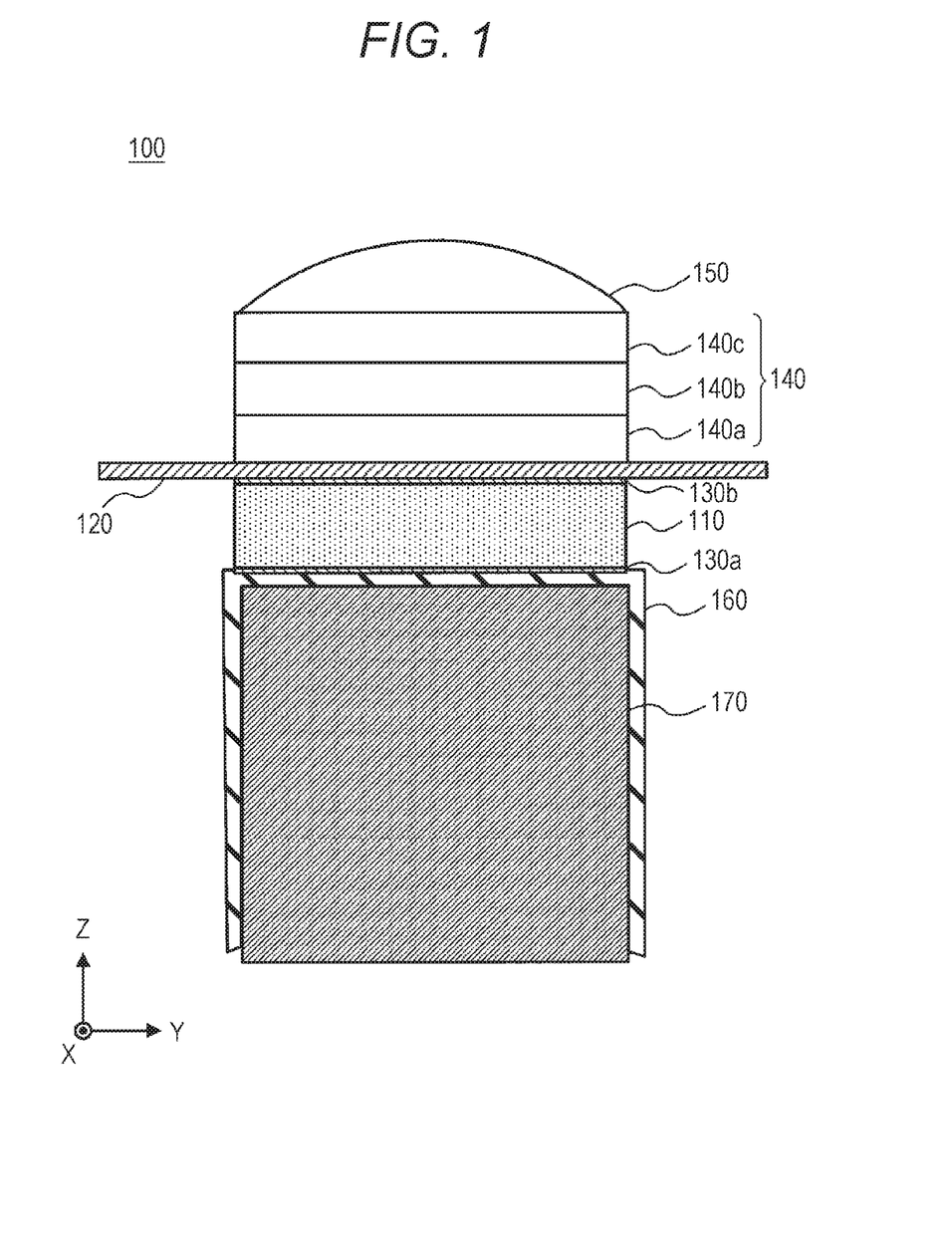
FIG. 1 is a cross-sectional view illustrating an example of an entire structure of an ultrasonic probe according to a first embodiment of the present invention.

FIG. 1 is a cross-sectional view illustrating an example of an entire structure of an ultrasonic probe 100 according to a first embodiment of the present invention.

As illustrated in FIG. 1, the ultrasonic probe 100 according to the first embodiment includes a piezoelectric element 110, a conductor layer 120 for applying a voltage to the piezoelectric element 110, signal electrodes 130a and 130b, an acoustic matching layer 140, an acoustic lens 150, a flexible printed circuit board (FPC) 160, and a back load material 170. In the ultrasonic probe 100, the conductor layer 120, the acoustic matching layer 140, and the acoustic lens 150 are laminated in this order from the piezoelectric element 110 to a subject, and the signal electrodes 130a and 130b, the FPC 160, and the back load material 170 are laminated in this order from the piezoelectric element 110 to the opposite side to the subject.

Incidentally, here, in each of members constituting the ultrasonic probe 100, a direction approaching a subject to be diagnosed is referred to as "upper surface side", and a direction moving away from the subject to be diagnosed is referred to as "back surface side".

In the ultrasonic probe 100 according to the first embodiment, the magnitude of an acoustic impedance changes stepwise in order of the piezoelectric element 110, the conductor layer 120, the acoustic matching layer 140, the acoustic lens 150, and a subject (living body). This makes reflection of an ultrasonic wave between the respective members less likely to occur, and makes it possible to improve resolution of a diagnostic image. The acoustic impedance of each member will be described later.

(Piezoelectric Element)

The piezoelectric element 110 is formed by arranging a plurality of piezoelectric bodies (not illustrated) that transmits an ultrasonic wave by application of a voltage one-dimensionally in an X direction in FIG. 1. The thickness of the piezoelectric element 110 can be, for example, 0.05 mm or more and 0.4 mm or less. Each of the piezoelectric bodies is formed of a piezoelectric ceramic such as lead zirconate titanate (PZT), a piezoelectric single crystal such as lead magnesium niobate/lead titanate solid solution (PMN-PT) or lead zirconate niobate/lead titanate solid solution (PZN-PT), a composite piezoelectric body obtained by combining these materials and a polymer material, or the like.

The magnitude of an acoustic impedance of the piezoelectric element 110 is usually 10 to 30 MRayls.

(Conductor Layer)

The conductor layer 120 is an electrode disposed on an upper surface side (a Z direction in FIG. 1 and a subject side) of the piezoelectric element 110 to apply a voltage to the piezoelectric element 110 together with the signal electrode 130b. The conductor layer 120 is bonded to a surface of the signal electrode 130b of the piezoelectric element 110 so as to make the conductor layer 120 electrically connected. For example, a method for electrical connection with the conductor layer 120 by bonding the conductor layer 120 with an extremely thin adhesive such as an epoxy resin, or a method for electrical connection with the conductor layer 120 by bonding the conductor layer 120 with a conductive adhesive is used, but any method may be used as long as electrical connection is possible. In the first embodiment, a lateral width (Y direction) of the conductor layer 120 is formed so as to be larger than a lateral width (Y direction and arrangement direction of piezoelectric element) of the piezoelectric element 110, and is grounded. The conductor layer 120 will be separately described in detail.

(Signal Electrode)

The signal electrodes 130a and 130b are disposed on an upper surface side and a back surface side (opposite surface to the surface on which the conductor layer 120 is disposed) of the piezoelectric element 110, and is an electrode for applying a voltage to the piezoelectric element 110 together with the conductor layer 120. The signal electrodes 130a and 130b can be formed by vapor-depositing or sputtering gold, silver, and the like, baking silver, or attaching a conductor such as copper to an insulating substrate and patterning the conductor.

(Acoustic Matching Layer)

The acoustic matching layer 140 is a layer for matching acoustic characteristics between the piezoelectric element 110 and the acoustic lens 150, and is generally formed of a material having an acoustic impedance substantially intermediate between that of the piezoelectric element 110 and that of the acoustic lens 150. The acoustic matching layer 140 generally includes a plurality of layers.

As illustrated in FIG. 1, in the first embodiment, the acoustic matching layer 140 includes a first acoustic matching layer 140a, a second acoustic matching layer 140b, and a third acoustic matching layer 140c. The magnitude of the acoustic impedance preferably gets smaller in order of the piezoelectric element 110, the first acoustic matching layer 140a, the second acoustic matching layer 140b, and the third acoustic matching layer 140c, and preferably gets smaller so as to approach the acoustic impedance of a subject (living body) in order from the first acoustic matching layer 140a having the closest acoustic impedance to the piezoelectric element 110. Here, the magnitude of the acoustic impedance of the first acoustic matching layer 140a is preferably 8 to 20 MRayls, and more preferably 10 to 15 MRayls. Examples of a material of the first acoustic matching layer 140a satisfying the above acoustic impedance include silicon, quartz, free-cutting ceramics, graphite filled with metal powder, and an epoxy resin filled with a filler such as metal or oxide.

The second acoustic matching layer 140b is laminated on an upper surface side of the first acoustic matching layer 140a. The magnitude of the acoustic impedance of the second acoustic matching layer 140b is preferably 3 to 12 MRayls. Examples of a material of the second acoustic matching layer 140b satisfying the above acoustic impedance include silicon, quartz, free-cutting ceramics, graphite filled with metal powder, and an epoxy resin filled with a filler such as metal or oxide.

The third acoustic matching layer 140c is laminated on an upper surface side of the second acoustic matching layer 140b. The magnitude of the acoustic impedance of the third acoustic matching layer 140c is preferably 1.9 to 8 MRayls. The third acoustic matching layer 140c satisfying the above acoustic impedance is formed of a plastic material mixed with a rubber material, a resin filled with silicone rubber powder, or the like.

Each layer of the acoustic matching layer 140 may be bonded with an adhesive usually used in the present technical field, such as an epoxy-based adhesive.

(Acoustic Lens)

The acoustic lens 150 focuses ultrasonic waves transmitted from the piezoelectric element 110 using refraction due to a difference in sound velocity between a subject (living body) and the acoustic lens 150 to improve resolution. As illustrated in FIG. 1, in the first embodiment, the acoustic lens 150 is a cylindrical acoustic lens extending in the Y direction in FIG. 1 and having a convex shape in the Z direction, focuses the ultrasonic waves in the Y direction, and emits the ultrasonic waves outside the ultrasonic probe 100. The acoustic lens 150 is formed of, for example, a soft polymer material having a sound velocity different from a living body.

Examples of the soft polymer material include a silicone rubber.

(Flexible Printed Circuit Board)

The flexible printed circuit board 160 is disposed in contact with a back surface side of the signal electrode 130a, and connects the signal electrode 130a to an external power supply or the like.

(Back Load Material)

The back load material 170 is a layer that holds the piezoelectric element 110 and attenuates an ultrasonic wave transmitted from the piezoelectric element 110 to a back surface side. The back load material 170 is usually formed of a synthetic rubber filled with a material for adjusting an acoustic impedance, a natural rubber, an epoxy resin, a thermoplastic resin, or the like. The shape of the back load material 170 is not particularly limited as long as being able to attenuate a transmitted ultrasonic wave.

The area of a surface of the back load material 170 in contact with the piezoelectric element 110 is preferably larger than that of the piezoelectric element 110 from a viewpoint of enhancing an attenuation efficiency of an ultrasonic wave transmitted from the piezoelectric element 110 to a back surface side.

(Conductor Layer)

As illustrated in FIG. 1, in the first embodiment, the conductor layer 120 is disposed between the piezoelectric element 110 and the first acoustic matching layer 140a. The magnitude of the acoustic impedance of the conductor layer 120 is between the magnitude of the acoustic impedance of the first acoustic matching layer 140a and the magnitude of the acoustic impedance of the piezoelectric element 110. Therefore, a material of the conductor layer 120 is preferably selected from materials having an acoustic impedance of 10 to 30 MRayls, and more preferably selected from materials having an acoustic impedance of 15 to 30 MRayls.

By making a difference in acoustic impedance between the conductor layer 120 and the piezoelectric element 110 or between the first acoustic matching layer 140a and the conductor layer 120 close to zero, reflection of an ultrasonic wave at these interfaces is less likely to occur, and resolution of a diagnostic image can be further improved.

An example of a material having an acoustic impedance of 10 to 30 MRayls is illustrated in Table 1.

The acoustic impedance can be calculated by the following formula (1).

$$\text{acoustic impedance (MRayls)} = \text{density (kg/m}^3\text{)} \times \text{sound velocity (m/sec)} \quad \text{Formula (1)}$$

TABLE 1

| Material | Acoustic impedance (MRayls) |
|---|---|
| Aluminum | 16.3 |
| Aluminum/SIC complex | 22.6 |
| Indium | 19.9 |
| Cadmium | 23.9 |
| Duralumin 17S | 17.6 |
| Zirconium | 30.0 |
| Titanium | 27.6 |
| Bismuth | 21.4 |
| Beryllium | 23.2 |
| Magnesium | 10.1 |
| Lead | 24.7 |
| Tin | 24.2 |
| Titanium alloy | Around 27 |

Among these materials, aluminum, indium, titanium, and a titanium alloy are preferable, and titanium and a titanium alloy are more preferable from viewpoints of availability, cost, and the like. Note that examples of the titanium alloy include an α+β type titanium alloy (Ti-6Al-4V, Ti-3Al-2.5V, Ti-6Al-4V-2Sn, or the like), a β type titanium alloy (Ti-15V-3Cr-3Sn-3Al, Ti-15Mo-5Zr-3Al, Ti-13V-11Cr-3Al, Ti-3Al-8V-6Cr-4Mo-4Zr, or the like), an α type titanium alloy (Ti-5Al-1 Mo+1V, Ti-5Al-2.5Sn, Ti-8Al-1Mo-1V, or the like), a near α type alloy (Ti-8Al-1Mo-1V or the like), and a near β type alloy (Ti-10V-2Fe-3Al or the like).

In the first embodiment, a material of the conductor layer 120 has high hardness to some extent in order to suppress generation of wrinkles and the like when a surface treatment of the material is performed before lamination between the piezoelectric element 110 and the first acoustic matching layer 140a. In addition, the material of the conductor layer 120 has a hardness that is not too high in order to make the conductor layer 120 less likely to be broken even when the conductor layer 120 is bent at the time of acting as a ground electrode. The material used as the conductor layer 120 preferably has a Vickers hardness (Hv) of 50 or more and 600 or less, and more preferably has a Vickers hardness (Hv) of 100 or more and 400 or less from the above viewpoint. By setting the Vickers hardness (Hv) of the conductor layer 120 to 50 or more and 600 or less, generation of wrinkles can be suppressed, high image quality can be obtained, and durability can be improved.

Here, the Vickers hardness (Hv) is calculated in accordance with JIS Z 2244 defined by Japanese Industrial Standards.

Tables 2 and 3 illustrate an example of a material having a Vickers hardness (Hv) of 50 or more and 600 or less.

TABLE 2

| Material | Vickers hardness (Hv) |
|---|---|
| Nickel | 96 |
| SCM 822 (chromium molybdenum steel) | 302 to 415 |
| Beryllium steel: after aging, C1720 (T) | 350 to 400 |
| SUS630 | 375 |
| Inconel (heat-resistant nickel alloy) | 150 to 280 |
| S45C (carbon steel for mechanical structure) | 201 to 269 |
| Hastelloy alloy (anticorrosive nickel alloy) | 100 to 230 |
| SUS304 | 187 |
| SUS430 | 183 |
| Cast iron | 160 to 180 |
| Aluminum alloy (7000 type, extra-super duralumin) | Around 155 |
| Brass | 80 to 150 |
| Pure iron | 110 |
| Hard platinum | Around 100 |
| Bronze | 50 to 100 |
| Aluminum alloy | 45 to 100 |
| Carbonyl iron | 56 to 80 |
| Magnesium alloy | 49 to 75 |
| Armco iron | 60 to 65 |
| Platinum (pure platinum) | Around 50 |

TABLE 3

| Material | Vickers hardness (Hv) |
|---|---|
| SUS430 | 150 |
| SUS301 | 165 |
| SUS304 | 150 |
| SUS316 | 145 |
| SUS310 | 185 |
| Hastelloy B | 210 |
| Hastelloy C | 210 |
| Inconel | 170 |
| Cobalt | 124 to 130 |
| Tungsten | 100 to 350 |
| Molybdenum | 147 |
| High carbon steel C % 0.8 to 1.6 | 180 to 280 |
| Nickel steel 40% Ni | 90 |

TABLE 3-continued

| Material | Vickers hardness (Hv) |
| --- | --- |
| Bronze | 65 to 70 |
| Nickel silver | 70 to 77 |
| Phosphor bronze | 74 to 80 |
| Titanium | 120 |
| Monel | 140 to 185 |
| Aluminum bronze | 120 |
| Duralumin | 115 to 128 |
| Brass (7:3) | 50 |
| SC material C % 0.4 to 0.5 | 150 |
| Titanium alloy | 110-320 |
| Titanium copper | 340-400 |

Among these materials, nickel, titanium, molybdenum, tungsten, and a titanium alloy are preferable, and titanium and a titanium alloy are more preferable from viewpoints of easiness of processing such as a surface treatment, availability, cost, and the like.

In the first embodiment, the conductor layer 120 may act as a ground electrode. At this time, the conductor layer 120 is formed so as to be larger than a lateral width (Y direction) of the piezoelectric element 110 in order to have a size capable of being grounded.

At this time, the material of the conductor layer 120 preferably has a small electric resistance. Specifically, the material used for the conductor layer 120 preferably has a specific electric resistance of $200 \times 10^{-6}$ ($\Omega \cdot cm$) or less, and more preferably has a specific electric resistance of $170 \times 10^{-6}$ ($\Omega \cdot cm$) or less. Here, as a method for measuring the electric resistance, for example, a four-terminal measurement method can be used. Note that the electric resistance can also be reduced by treating a surface of the conductor layer with gold plating or the like.

Table 4 illustrates an example of a material having a specific electric resistance of $200 \times 10^{-6}$ ($\Omega \cdot cm$) or less.

TABLE 4

| Material | Electric resistance ($10^{-6}$ ($\Omega \cdot cm$)) |
| --- | --- |
| Aluminum | 2.8 |
| Beryllium | 6.1 |
| Chromium | 12.7 |
| Copper | 1.7 |
| Gold | 2.4 |
| Iron | 10.2 |
| Lead | 20.8 |
| Manganese | 185.4 |
| Mercury | 9.7 |
| Molybdenum | 5.3 |
| Monel | 44.2 |
| Brass 70-30 | 6.3 |
| Antimony | 39.4 |
| Nichrome | 108.0 |
| Nickel | 6.9 |
| Platinum | 9.9 |
| Silver | 1.6 |
| Steel | 12.7 |
| Stainless | 73.7 |
| SUS410 | 62.2 |
| Tin | 11.4 |
| Titanium | 53.3 |
| Tungsten | 5.6 |
| Uranium | 32.0 |
| Zirconium | 40.6 |
| Titanium alloy | Around 140 to 170 |
| Titanium copper | 17.2 |

Among these materials, aluminum, copper, gold, molybdenum, nickel, silver, tungsten, titanium, and a titanium alloy are preferable, and titanium and a titanium alloy are more preferable from viewpoints of availability and cost.

The material of the conductor layer 120 is preferably titanium or a titanium alloy because titanium and a titanium alloy satisfy all the above-described conditions of acoustic impedance, Vickers hardness (Hv), and specific electric resistance.

(Method for Cleaning Conductor Layer)

The ultrasonic probe 100 is required to be durable because the ultrasonic probe 100 is used repeatedly for an examination or the like. In addition, the ultrasonic probe 100 is formed of a plurality of different materials, and therefore each of the materials is required to have adhesive strength to such an extent that each of materials can withstand processing during manufacturing. Here, a surface of the conductor layer 120 is preferably cleaned in order to enhance durability and adhesive strength. Examples of a cleaning method include vacuum cleaning, degassing cleaning, wiping cleaning, ultrasonic cleaning, immersion cleaning, jet cleaning, spray cleaning, and shower cleaning using, as a cleaning solution, a hydrocarbon-based solution (a normal paraffin, an isoparaffin, a naphthene, an aromatic compound, or the like), a solvent-based solution (acetone, isobutyl alcohol, isopropyl alcohol, isopropyl alcohol, ethanol, methanol, benzene, dichloromethane, hexane, or the like), an aqueous solution (an acidic cleaner, a neutral cleaner, an alkaline cleaner, or the like formed of an inorganic/organic builder, a surfactant, a chelating agent, or an anticorrosive agent), a chlorine-based solution (trichloroethylene, dichloromethane, perchloroethylene, or the like), a fluorine-based solution (a perfluorocarbon, a hydrochlorofluorocarbon, a hydrofluorocarbon, a cyclic fluorine-based solvent, a hydrofluoroether, or the like), or a bromine-based solution (1-bromopropane or the like). In addition, plasma cleaning ($O_2$, argon, or the like) may be performed. After cleaning, hot air drying, radiation heating drying, rotation (spin) drying, air blow drying, reduced pressure drying (vacuum drying), natural drying, wiping drying, or the like is performed.

(Surface Treatment of Conductor Layer)

The conductor layer 120 may be subjected to a primer treatment or the like in order to improve an adhesive property. In addition, a lamination surface of the conductor layer 120 on an upper surface side and/or a back surface side has been preferably subjected to a surface treatment in order to improve not only an adhesive property but also electric conductivity. Examples of the surface treatment include a method for vapor-depositing or sputtering gold, silver, and the like, and a method for baking silver.

(Relationship Between Thickness of Conductor Layer and Specific Band of Frequency)

The following description will be made by assuming that the sound velocity in the conductor layer 120 is represented by v, the transmission frequency (center frequency) is represented by f, and $\lambda = v/f$ is satisfied. Note that the transmission frequency (center frequency) is the center frequency of a bandwidth that is −6 dB with respect to an intensity peak of a transmission ultrasonic wave.

The conductor layer 120 may have a function as an acoustic matching layer. In a case where the conductor layer 120 has a function as an acoustic matching layer, the thickness of the acoustic matching layer is preferably $\lambda/4$. However, the thickness of the acoustic matching layer may be slightly deviated from $\lambda/4$ depending on desired characteristics.

Figure 3:
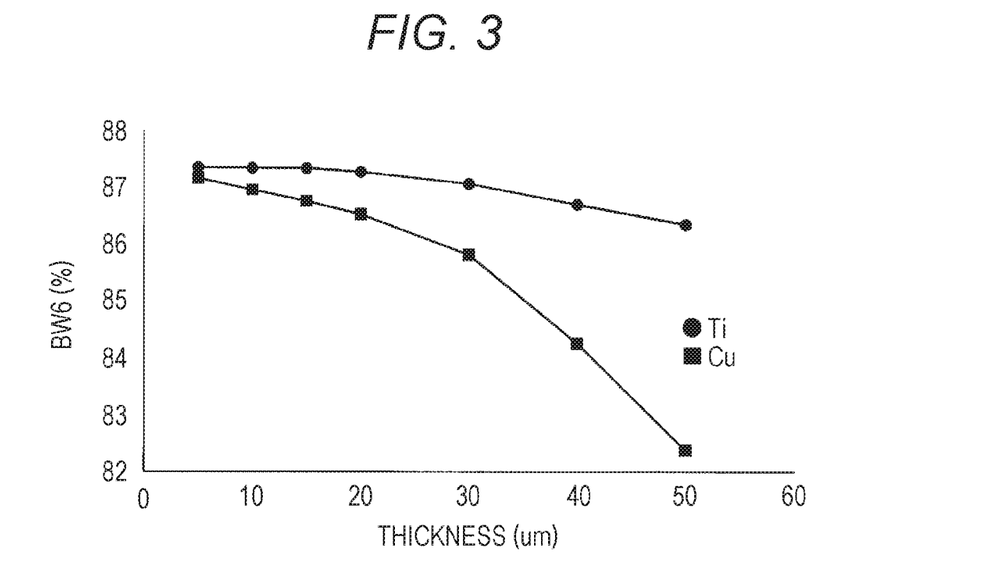
FIG. 3 is a graph illustrating a relationship between the thickness of a conductor layer and a specific band of a frequency when the conductor layer is disposed between a piezoelectric element and a first acoustic matching layer as in FIG. 1.

FIG. 3 is a graph illustrating a relationship between the thickness of the conductor layer 120 and a specific band of a frequency that is −6 dB with respect to maximum sensitivity when the conductor layer 120 is disposed between the piezoelectric element 110 and the first acoustic matching layer 140a, and calculation is performed using a time domain finite element method with a center frequency of 7 MHz in the configuration of FIG. 1. Here, the vertical axis in FIG. 3 indicates a specific band (%) of a frequency that is −6 dB with respect to maximum sensitivity, and the horizontal axis indicates the thickness (μm) of the conductor layer 120.

FIG. 3 illustrates a specific band (%) of a frequency that is −6 dB when a copper foil (with an acoustic impedance of 41.8 MRayls) and a titanium foil (with an acoustic impedance of 27.6 MRayls) are selected as the conductor layer 120, and the thicknesses thereof are 5, 10, 15, 20, 30, 40, and 50 μm.

As illustrated in FIG. 3, when a material used as the conductor layer 120 is a titanium foil, even when the thickness is $\lambda/30$ (about 29 μm), there is no large difference from a value of a specific band of a frequency that is −6 dB at a thickness of $\lambda/90$ (about 9.6 μm). Meanwhile, in a case of a copper foil, when the thickness is $\lambda/22$ (about 30 μm) or more, a value of a specific band of a frequency that is −6 dB starts to fall sharply. That is, in the case of a titanium foil, even when the thickness of the conductor layer 120 is increased, a frequency band of the ultrasonic probe 100 can be broadened. This indicates that a selection range of the thickness of the conductor layer 120 is wide when a titanium foil is used as the conductor layer 120.

Meanwhile, in the case of a copper foil, as illustrated in FIG. 3, a value of a specific band of $\lambda/90$ (about 7.5 μm) to $\lambda/22$ (about 30 μm) decrease as the thickness of the copper foil increases. Therefore, in the case of a copper foil, it is necessary to manufacture the conductor layer 120 having a thin thickness. However, a copper foil has a low hardness, may be easily wrinkled, and is not suitable for manufacturing the conductor layer 120 having a thickness of $\lambda/90$ (about 7.5 μm) or less. Meanwhile, in the case of a titanium foil, a value of a specific band of a thickness of $\lambda/90$ (about 9.6 μm) to $\lambda/30$ (about 29 μm) does not change largely, a selection range of the thickness of the conductor layer 120 is wide, and therefore the conductor layer 120 having a thinner or thicker thickness than a copper foil can also be easily manufactured.

Here, the total thickness of all the members forming the ultrasonic probe 100 is preferably thin. Therefore, in the case of using a titanium foil, the conductor layer 120 preferably has a thickness of $\lambda/300$ to $\lambda/30$, and more preferably has a thickness of $\lambda/300$ to $\lambda/40$. This makes it possible to improve performance of the ultrasonic probe while suppressing generation of wrinkles and a large change in a specific band.

A method for converting the thickness of the conductor layer 120 is as follows. First, regarding a copper foil (sound velocity: 4700 m/s), when the center frequency of an ultrasonic wave to be transmitted and received is 7 MHz, the wavelength of the ultrasonic wave in the copper foil is about 670 μm. The thickness of the copper foil at $\lambda/90$ is calculated is to be about 7.5 μm. Similarly, a titanium foil (sound velocity: 6070 m/s) has a thickness of about 9.6 μm at $\lambda/90$. Here, based on a specific band of a frequency that is −6 dB when the thickness of a copper foil is $\lambda/90$ (about 9.6 μm), in the case of a titanium foil, it is found that the same specific band as the copper foil can be obtained even when the thickness is increased to $\lambda/30$ (about 30 μm).

As described above, by using a titanium foil or a titanium alloy as a material of the conductor layer 120, a difference in acoustic impedance from the piezoelectric element 110 to a subject (living body) can be reduced stepwise. In addition, by using a titanium foil or a titanium alloy as a material of the conductor layer 120, the usable thickness of the conductor layer 120 can be selected in a range of $\lambda/300$ to $\lambda/30$. In addition, the hardness of each of titanium and a titanium alloy is higher than the hardness of a copper foil. Therefore, even when the thickness of the conductor layer 120 is reduced, in a surface treatment step, generation of wrinkles can also be suppressed, for example, during vapor deposition, sputtering, or bonding of members.

[Second Embodiment]
(Configuration of Ultrasonic Probe)

Figure 2:
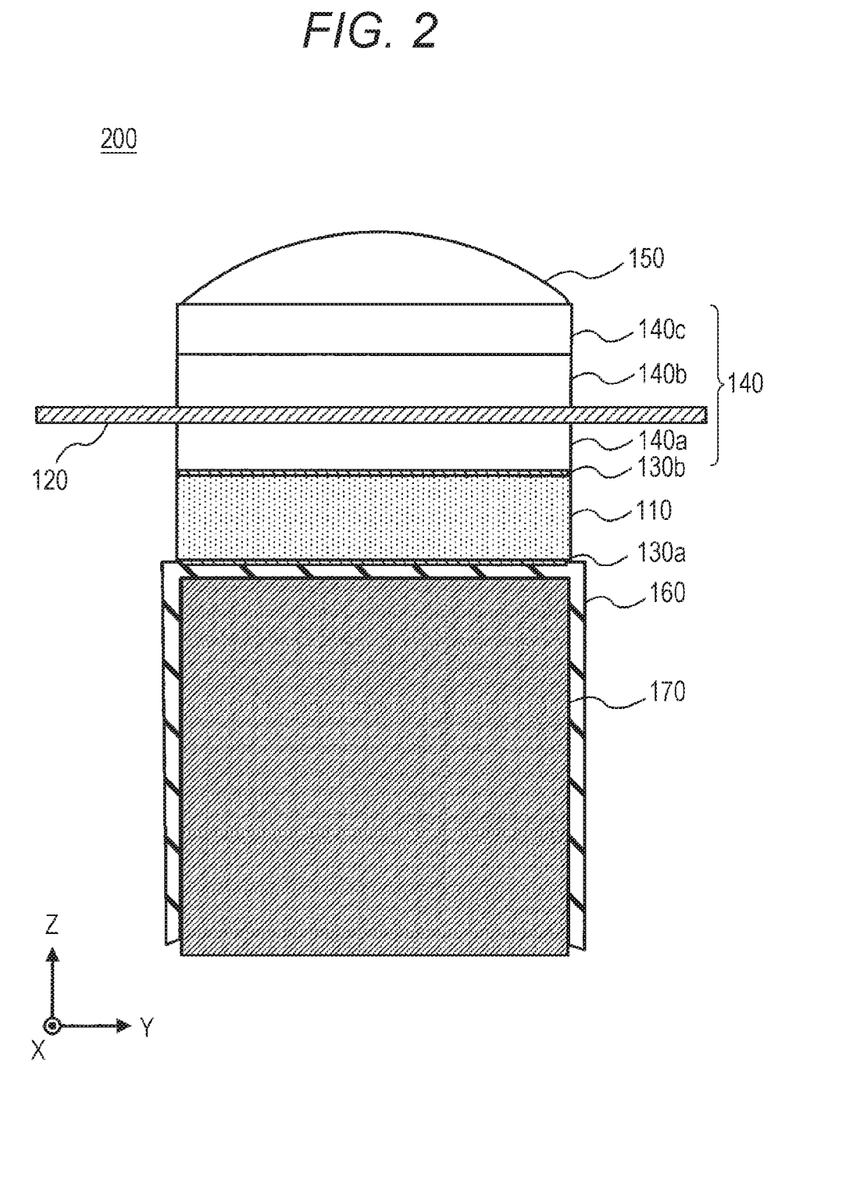
FIG. 2 is a cross-sectional view illustrating an example of an entire structure of an ultrasonic probe according to a second embodiment of the present invention.

An ultrasonic probe 200 according to a second embodiment is different from the ultrasonic probe 100 according to the first embodiment in a position where a conductor layer 120 is laminated. Therefore, the same components as those of the ultrasonic probe 100 according to the first embodiment are denoted by the same reference numerals, and description thereof is omitted.

FIG. 2 is a cross-sectional view illustrating an example of an entire structure of the ultrasonic probe 200.

As illustrated in FIG. 2, the ultrasonic probe 200 is different from the ultrasonic probe 100 according to the first embodiment in that the conductor layer 120 is disposed between a first acoustic matching layer 140a and a second acoustic matching layer 140b.

(Conductor Layer)

As illustrated in FIG. 2, in the second embodiment, the conductor layer 120 is laminated between the first acoustic matching layer 140a and the second acoustic matching layer 140b.

Figure 4:
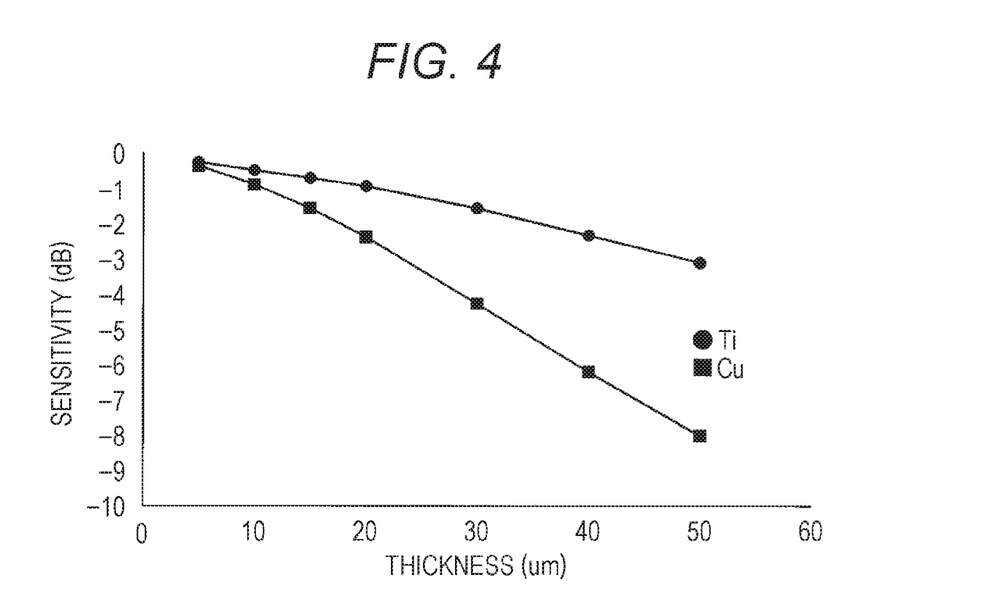
FIG. 4 is a graph illustrating a relationship between the thickness of a conductor layer and sensitivity (dB) when the conductor layer is disposed between a first acoustic matching layer and a second acoustic matching layer as in FIG. 2.

The magnitude of an acoustic impedance of the conductor layer 120 is preferably between the magnitude of the acoustic impedance of the first acoustic matching layer 140a and the magnitude of the acoustic impedance of the second acoustic matching layer 140b. Therefore, the magnitude of the acoustic impedance of the conductor layer 120 is preferably 10 to 20 MRayls. As illustrated in Table 1, aluminum and indium are desirable from a viewpoint of the acoustic impedance. However, aluminum and indium do not have sufficient hardness which is one of the characteristics of the present invention, and are not practically used. However, for example, duralumin described in Tables 1 and 2 has an acoustic impedance of 17.6 in a range of 10 to 20 MRayls and has a Vickers hardness (Hv) of 115 to 128 in a range of 50 or more and 600 or less, satisfying both the characteristics. Therefore, duralumin is preferable. However, even if the conductor layer has an acoustic impedance of 20 MRayls or more, as illustrated in FIG. 4, if the thickness of a titanium foil is $\lambda/40$ (about 20 μm) or less, sensitivity deterioration is about 1 dB, and the acoustic characteristics are not affected, causing no problem. Incidentally, in this verification, the conductor layer 120 is disposed between the first acoustic matching layer 140a and the second acoustic matching layer 140b in the configuration of FIG. 2, and calculation is performed using a time domain finite element method with a center frequency of 7 MHz.

As illustrated in FIG. 4, the vertical axis indicates maximum sensitivity (dB), and the horizontal axis indicates the thickness (μm) of the conductor layer 120. In addition, FIG. 4 illustrates maximum sensitivity (dB) when a copper foil (with an acoustic impedance of 41.8 MRayls) and a titanium foil (with an acoustic impedance of 27.6 MRayls) are selected as the conductor layer 120, and the thicknesses thereof are 5, 10, 15, 20, 30, 40, and 50 μm. Note that the conductor layer 120 has a Vickers hardness (Hv) of 50 or more and 600 or less.

Note that the conductor layer 120 may act as a ground electrode also in the second embodiment. At this time, the conductor layer 120 is formed so as to be larger than a lateral width (Y direction) of the piezoelectric element 110 in order to have a size capable of being grounded.

In the second embodiment, when the first acoustic matching layer 140a is formed of a non-conductive material, the vicinity of the material of the first acoustic matching layer 140a may be subjected to an electrode treatment, or a through hole or the like may be formed in the first acoustic matching layer 140a.

In the second embodiment, the conductor layer 120 may be laminated between the second acoustic matching layer 140b and a third acoustic matching layer 140c.

(Ultrasonic Diagnostic Apparatus)

Figure 5:
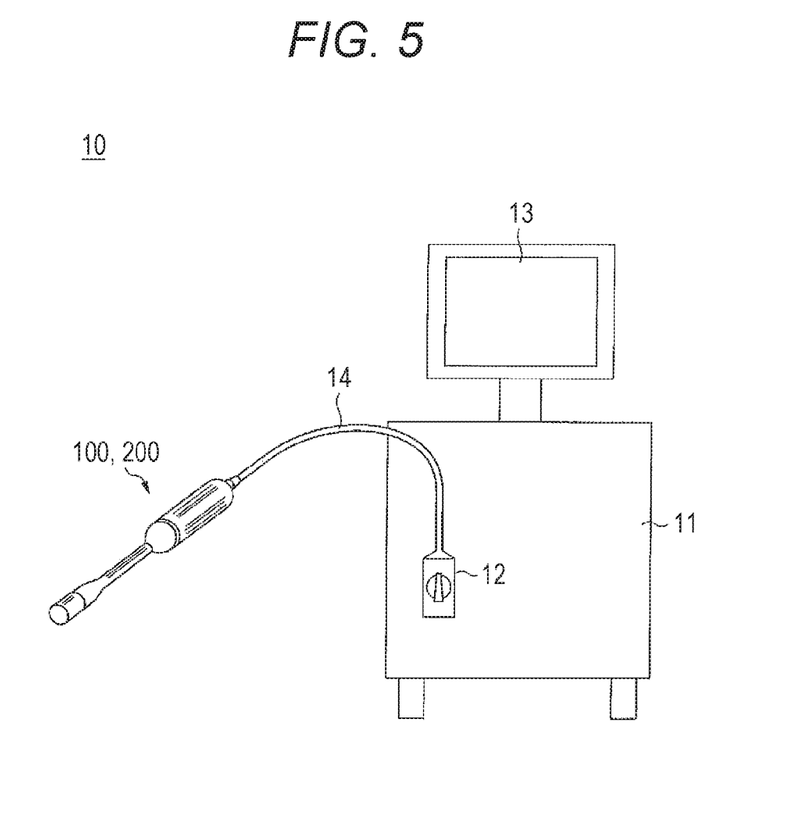
FIG. 5 is a schematic view illustrating an example of an ultrasonic diagnostic apparatus including an ultrasonic probe according to an embodiment of the present invention.

FIG. 5 is a schematic view illustrating an example of an ultrasonic diagnostic apparatus 10 including the ultrasonic probe 100 or the ultrasonic probe 200. The ultrasonic diagnostic apparatus 10 includes the ultrasonic probe 100 or 200, a main body 11, a connector 12, and a display 13.

The ultrasonic probe 100 or 200 is connected to the ultrasonic diagnostic apparatus 10 via a cable 14 connected to the connector 12.

An electric signal (transmission signal) from the ultrasonic diagnostic apparatus 10 is transmitted to the piezoelectric element 110 of the ultrasonic probe 100 or 200 via the cable 14. The transmission signal is converted into an ultrasonic wave in the piezoelectric element 110 and transmitted into a living body. The transmitted ultrasonic wave is reflected by a tissue or the like in the living body. A part of the reflected wave is received again by the piezoelectric element 110, converted into an electric signal (reception signal), and transmitted to the main body 11 of the ultrasonic diagnostic apparatus 10. The reception signal is converted into image data in the main body 11 of the ultrasonic diagnostic apparatus 10 and displayed on the display 13.

Each of the ultrasonic diagnostic apparatuses according to the above embodiments includes the ultrasonic probe according to an embodiment of the present invention in which a difference in acoustic impedance from a piezoelectric material to a subject (living body) is gradually reduced, and therefore can generate an ultrasonic image having higher image quality.

Note that each of the above embodiments describes the ultrasonic probe including a back load material, but the ultrasonic probe does not need to include the back load material. In addition, a material having an acoustic impedance equal to or higher than PZT may be disposed between the PZT and a back load material, and an ultrasonic wave directed to a back surface side may be reflected to be superposed on an ultrasonic wave directed to an upper surface side.

The present invention is useful as an ultrasonic probe of an ultrasonic apparatus for obtaining an ultrasonic image with high sensitivity and high image quality because of being able to broaden a probe frequency band.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasonic probe comprising:
   a piezoelectric element that transmits and receives an ultrasonic wave;
   one or a plurality of acoustic matching layers disposed on a subject side of the piezoelectric element; and
   a conductor layer that applies a voltage to the piezoelectric element, wherein
   the conductor layer is disposed between the piezoelectric element and the acoustic matching layer, or between a first acoustic matching layer and a second acoustic matching layer of the plurality of acoustic matching layers,
   a magnitude of an acoustic impedance of the conductor layer is between a magnitude of an acoustic impedance of the piezoelectric layer and a magnitude of an acoustic impedance of the acoustic matching layer or between a magnitude of an acoustic impedance of the first acoustic matching layer and a magnitude of an impedance of the second acoustic matching layer, and
   the conductor layer has a Vickers hardness (Hv) of 50 or more and 600 or less.

2. The ultrasonic probe according to claim 1, wherein a magnitude of an acoustic impedance of the conductor layer is between a magnitude of an acoustic impedance of a layer disposed in contact with one surface of the conductor layer and a magnitude of an acoustic impedance of a layer disposed in contact with the other surface of the conductor layer.

3. The ultrasonic probe according to claim 1, wherein the conductor layer acts as a ground electrode.

4. The ultrasonic probe according to claim 1, wherein the conductor layer has a thickness of $\lambda/30$ or less when a sound velocity in the conductor layer is represented by v, a center frequency of an ultrasonic wave to be transmitted by the piezoelectric element is represented by f, and $\lambda$ is represented by v/f.

5. The ultrasonic probe according to claim 1, wherein the conductor layer has a function as an acoustic matching layer.

6. The ultrasonic probe according to claim 1, wherein at least one of the one surface and the other surface in the conductor layer has been subjected to a surface treatment.

7. The ultrasonic probe according to claim 1, wherein the conductor layer contains titanium or a titanium alloy.

8. The ultrasonic probe according to claim 1, wherein the conductor layer is formed of titanium or a titanium alloy.

9. An ultrasonic diagnostic apparatus comprising the ultrasonic probe according to claim 1.

10. The ultrasonic probe according to claim 1, wherein the magnitude of the acoustic impedance of the conductor layer is 10-30 MRayl.

* * * * *